US007060453B1

(12) United States Patent
Fish

(10) Patent No.: US 7,060,453 B1
(45) Date of Patent: Jun. 13, 2006

(54) METHOD AND KIT FOR THE DETERMINATION OF ANALYTE CONCENTRATION IN BLOOD

(76) Inventor: Falk Fish, 4, Eliahu Hakim Street, Apt. 12, 69120 Tel Aviv (IL)

( * ) Notice: Subject to any disclaimer, the term of this patent is extended or adjusted under 35 U.S.C. 154(b) by 0 days.

(21) Appl. No.: 09/763,415

(22) PCT Filed: Aug. 19, 1999

(86) PCT No.: PCT/IL99/00447

§ 371 (c)(1),
(2), (4) Date: May 16, 2001

(87) PCT Pub. No.: WO00/11469

PCT Pub. Date: Mar. 2, 2000

(30) Foreign Application Priority Data

Aug. 21, 1998 (IL) .................................. 125880

(51) Int. Cl.
*C12Q 1/54* (2006.01)
*C12Q 1/00* (2006.01)
*A01N 1/02* (2006.01)
*A61K 39/00* (2006.01)
*A61K 45/00* (2006.01)

(52) U.S. Cl. .................... 435/14; 424/278.1; 435/2; 435/4; 435/7.95; 435/69.6; 436/66; 436/164; 436/172; 436/177; 436/519; 436/520; 436/522

(58) Field of Classification Search ............... 435/2, 435/4, 7.1, 72, 7.24, 725, 7.8, 7.92–7.95, 435/8, 12, 14, 28, 183, 69.6, 283.1, 287.1, 435/288.1; 436/14, 66, 164, 172, 177, 519, 436/520, 521, 522, 807, 808, 810; 424/278.1
See application file for complete search history.

(56) References Cited

U.S. PATENT DOCUMENTS

| 3,975,161 | A |   | 8/1976  | Svoboda et al. |       |
|-----------|---|---|---------|----------------|-------|
| 4,017,261 | A |   | 4/1977  | Svoboda et al. |       |
| 4,615,982 | A |   | 10/1986 | Lawrence       |       |
| 5,056,521 | A |   | 10/1991 | Parsons et al. |       |
| 5,089,420 | A | * | 2/1992  | Albarella et al. | 436/66 |
| 5,268,148 | A |   | 12/1993 | Seymour        |       |
| 5,362,307 | A |   | 11/1994 | Guy et al.     |       |

FOREIGN PATENT DOCUMENTS

| WO | WO 91/13355 A2 |   | 9/1991  |
|----|----------------|---|---------|
| WO | WO 91/13355    | * | 9/1995  |
| WO | WO 95/27205    | * | 10/1995 |
| WO | WO 95/27205 A1 |   | 10/1995 |
| WO | WO 99/22639    |   | 5/1999  |

OTHER PUBLICATIONS

Ben-Aryeh et al. 1988. J. Diabet. Complications. 2:96-99.*
Paisey et al. 1984. British Medical Journal. (288): 669-671.*
Sigma Chemical Company Catalog. 1992. Biochemical Organic Compounds for Research and Diagnostic Reagents.*
Paisey et al. 1984. British Medical Journal. vol. 288, pp. 669-671.*
Jablonski et al., "Properties and Uses of Immobilized Light-Emitting Enzyme Systems from *Beneckea harveyi*", *Clinical Chemistry*, 1979, p. 1622-1627, vol. 25, No. 9.
Piazza et al., "Blood in Saliva of HIV Seropositive Drug Abusers: Possible Implication in AIDS Transmission", *Boll Soc. Ital. Biol. Sper.*, 1991, p. 1047-1052. vol. 67, No. 12.
Lentner, ed. *Geigy Scientific Tables*, 1980. p. 95-96, vol. 1, Ciba-Geigy, Basle, Switzerland.
Sakita et al., "Three-dimensional Microvasculature of the Hair Follicle", *Journal of Dermatological Science*, 1994, p. S1-S4, vol. 7.
Keating et al., "What's in a Name?—Medical Samples and Scientific Evidence in Sexual Assaults", *Med. Sci. Law*, 1994, p. 187-201. vol. 34.
Song, "Examinations of ABO Bloodgroups of Human Hair", *Forensic Science International*, 1988, p. 173-177, vol. 36.
Ben-Aryeh et al., "Salivary composition in Diabetic Patients", *J. Diabet. Complications*, 1988, p. 96-99, vol. 2.
Forbat et al., "Glucose Concentrations in Parotid Fluid and Venous Blood of Patients Attending a Diabetic Clinic", *Journal of the Royal Society of Medicine*, 1981, p. 725-728, vol. 74.
Patrick et al., "Home Glucose Monitoring in Type 2 Diabetes: Is It a Waste of Time?", *Diabet. Med.*, 1994, p. 62-65, vol. 11.
Sönksen, "Home Monitoring of Blood Glucose by Diabetic Patients", *Acta Endocrinologica*, 1980, p. 145-153, vol. 238.
Kimes et al., "Erythrocyte Acid Phosphatase in Human Hair Root Sheaths", *J. Forensic Sci.*, 1984, p. 64-66, vol. 29.
Piazza et al., "Passionate Kissing and Microlesions of the Oral Mucosa: Possible Role in AIDS Transmission", *Jama*, Jan. 13, 1989, p. 244-245, vol. 261, No. 2.
Haggerty et al., "Continuous Monitoring of Reactions that Produce NADH and NADPH using Immobilized Luciferase and Oxidoreductases from *Beneckea harveyi*", *Analytical Biochemistry*, 1978, p. 162-173, vol. 88.
*Geigy Scientific Tables*, 8th Edition, Ciba-Geigy Publication, Basle, Switzerland, ISBN 0-914168-50-9 (1980).

* cited by examiner

*Primary Examiner*—Lynette R. F. Smith
*Assistant Examiner*—J. Hines
(74) *Attorney, Agent, or Firm*—Browdy and Neimark, PLLC

(57) ABSTRACT

A method is provided for determining the level of an analyte in the blood of an individual based on determination of the level of the same analyte in non-blood sample (e.g. urine, saliva and hair) obtained from the individual. The non-blood sample contains red blood cells and the volume of the blood in the sample together with the amount of the analyte in the sample are the basis for calculating the level of the analyte in the individual's blood. Kits for carrying out the above method are also provided.

3 Claims, No Drawings

METHOD AND KIT FOR THE DETERMINATION OF ANALYTE CONCENTRATION IN BLOOD

The present application is the national stage under 35 U.S.C. 371 of international application PCT/IL99/00447, filed 19 Aug. 1999, which designated the United States, which international application was published under PCT Article 21(2) in English.

FIELD OF THE INVENTION

This invention concerns a method for determining the concentration of various analytes in the blood of an individual and kits for carrying out the method of the invention.

PRIOR ART

The following is a list of prior art publications referred to in the present specification:
1. Guy and Rao, U.S. Pat. No. 5,362,307.
2. Sönsken P H, *Acta Endocrinol. Suppl.* (Copenhagen) 238:145–155 (1980).
3. Patrick, A. W., et al., *Diabet. Med.*, 11:62–65 (1994).
4. Forbat, L. N., et al., *J.R. Soc. Med.*, 74:725–728 (1981).
5. Ben-Aryeh, H., et al., *J. Diabet. Complications*, 2:96–99 ((1988).
6. PCT Application Publication No. WO 99/22639
7. Song, S. J. *Forensic Sci. Int.*, 36:173–7 (1988).
8. Keating, S. M., Allard, J. E., *Med. Sci. Law*, 34:187–201 (1994).
10. Geigy Scientific Tables, $8^{th}$ Edition, Ciba-Geigy Publication, Basle, Switzerland, ISBN 0-914168-50-9 (1980).
11. Kimes, D. R., et al., *J. Forensic Sci.*, 29:64–66 (1984)
12. Sakita, S., et al., *Dermatol. Sci.*, 7 Suppl: S1–4 (1994).
13. U.S. Pat. No. 5,268,148.

The acknowledgement herein of the above art should not be construed as an indication that this art is in any way relevant to the patentability of the invention as defined in the appended claims.

The above publications will be acknowledged in the following by indicating their number from the above list.

BACKGROUND OF THE INVENTION

There are many circumstances in which it is necessary to determine the level of one or more analytes in the blood of an individual at a given point in time. Often, a low volume blood sample extracted from the individual is sufficient for obtaining the required information. Such low volume blood samples are especially suitable in conditions wherein it is necessary to obtain a blood sample from the individual frequently, such as in the case of diabetic patients. Several years ago, a ten year long diabetes care and complications trial (DCCT) showed that the preferred mode of treatment of insulin dependent diabetes (Type 1) was by frequent small-dose administrations of insulin to such patients and determining the glucose level after each such administration. To follow such a treatment, a diabetic patient is required to puncture his skin and obtain a drop of blood for the glucose test at least three times a day. Such a frequent and repetitive puncturing is painful and often results in infection and formation of hard scar tissue and as a result, many diabetic patients neglect to sufficiently test their glucose level.

In an attempt to minimize the harm or pain caused by various techniques routinely used for obtaining a body fluid, several minimally invasive or non-invasive methods for determining the concentration of a substance in the blood by obtaining and analyzing a body fluid have been developed in which a very small sample of body fluid is obtained. Guy and Rao[1] have shown a method for determining the concentration of an inorganic or organic substance in an individual by obtaining an interstitial fluid sample from the individual by a process called iontophoresis. In accordance with this method, an electric field is employed which causes migration of ions which carry with them non-charged molecules, e.g. glucose.

Another minimally invasive method for obtaining a body fluid is that of SpecRx, Inc. Norcross, Ga., USA. A minute and shallow round hole is created in the skin, extending just below the stratum corneum and a sample of interstitial fluid is collected through this hole. That fluid is then tested for its glucose content by one of the methods known in the art.

In such minimally invasive methods the concentration of the tested substance in the obtained interstitial fluid sample often does not correctly indicate the level of the same substance in the blood of the tested individual at the time in which the sample was obtained or shortly thereafter. This is mostly due to the fact that the concentration of the tested substance varies in different locations in the body and at different hours of the day, and therefore, the concentration of a certain analyte in a body fluid other than the blood itself may significantly differ from its concentration in the blood at the same time. Moreover, although the side effects of such minimally invasive methods are reduced in comparison to some conventional methods for obtaining a blood sample, they still often result in discomfort to the tested individual, and involve wounding of the skin, and in some cases even disruption of blood vessels.

Attempts to detect the correct glucose level in the blood by determining the level of glucose in fluids of body samples other than blood such as saliva, urine or tears were found to be non suitable since the concentration of the glucose in such fluids was shown to be variable and, more often than not, did not directly reflect the concentration of the glucose in the blood at the relevant point in time[2-6].

Hair has also been used to detect the existence of various substances in a tested individual. The detection of a certain substance in the hair, obtained from an individual, provides evidence and information on the existence of the same substance in the tested individual at a certain, unknown period of time, i.e. that the individual was exposed at some time or another to the substance. Methods based on analysis of hair have been used, for example, in forensic medicine to determine whether an individual has, some time in the past, been exposed to drugs, for determining ABO blood groupings[7] (e.g. as evidence in cases of sexual assaults[8]) etc.

The percent of protein glycation (i.e. binding of glucose to protein) in hair specimens has also been used to obtain information on the tested individual from which the hair specimen was obtained. The growth rate of hair is relatively high and therefore it is possible to compare the level of glycated protein in the older part of the hair closer to the level of the glycated protein in the newer part of the hair (closer to the root). A higher level of glycated protein in the newer part of the hair may, in some cases, indicate the development of a certain condition in an individual e.g. to predict the possible onset of diabetes[9].

All the above methods provide general information which enables to determine whether a tested individual was ever exposed to a substance of interest. Such methods have not been used for determining the level of a desired substance in the blood of the tested individual at the time in which the hair was obtained.

It has been shown that some of the above mentioned body samples, including urine, saliva or hair roots contain red blood cells[10-12].

SUMMARY OF THE INVENTION

In accordance with the present invention, it has been realized that it may be possible to determine the concentration of various analytes in an individual's blood by obtaining a sample from the individual which is a non-blood sample but which contains within it red blood cells and determining the concentration of the analyte in the blood or blood cells present in such a sample. In accordance with the invention it was realized for the first time that such samples are a readily available source for blood or red blood cells which may be useful in determining the level of analytes of interest in the blood of an individual.

The concentration of various analytes, and specifically of glucose, in the red blood cell is lower than their concentrations in the plasma, however, it is always at a constant ratio to the concentration of the analyte in the plasma. Therefore, by determining the concentration of glucose or any other analyte in the red blood cells present in the non-blood body samples, it is possible to calculate and determine the concentrations of the measured analyte in the blood of the individual from which these samples were obtained.

By its first aspect, the present invention thus provides a method for determining the level of an analyte in the blood of an individual comprising:
 (i) obtaining a sample from said individual, said sample being a non-blood sample but containing blood components;
 (ii) determining the volume of blood in the obtained sample by measuring the level of a blood component in said samples;
 (iii) determining the amount of said analyte in the sample or in the blood cells present in said non-blood sample; and
 (iv) calculating the level of said analyte in the blood of the tested individual based on the measurements in (ii) and (iii).

The term "level" as it is to be understood in the context of the present invention relates either to a quantity or to the concentration of the tested analyte.

An analyte may be any substance or component found in the blood for example, sugars, proteins, organic compounds etc., which is present in detectable amounts in the non-blood fluid or sample.

The volume of blood in the obtained body or sample is measured as a basis for calculating the concentration of the analyte in the blood. Measurement of the blood volume is based on determining the amount of a blood component in the sample.

The term "sample" relates to any fluid or non-fluid (e.g. tissue or cells) which is obtained from an individual and which contains within it red blood cells.

Preferably, the non-blood sample is obtained by non-invasive or minimally invasive methods. The terms "non-invasively" or "minimally invasive" relate to any method for obtaining a body fluid sample which does not involve penetration of the inner layers of the skin of the individual with a sharp tool or with evaporating radiation (e.g. laser irradiation).

By a preferred embodiment of the invention, the volume of the blood will be determined by measuring the amount of hemoglobin in the obtained sample by any of the methods known in the art (e.g. Piazza et al., Boll Soc. *Ital. Biol. Sper* 67:1047–1052, 1991; Piazza et al, *JAMA* 4 261:244–245, 1989). Examples of such methods are methods relying on the peroxidase activity of hemoglobin which incorporate a chromogenic or luminescent signal imparting high sensitivity (see Example 2 below). Hemoglobin in body samples can also be detected and quantified by commercially available dry chemistry test strips, which rely on calorimetric reaction of hemoglobin with peroxides, such as those described in U.S. Pat. Nos. 4,615,982, 3,975,161 and 4,017,261, assigned to Lachema a.s., Brno, Czech Republic and in U.S. Pat. No. 5,089,420 assigned to Miles, Elkhart, Ind., USA. Other methods for determining the level of hemoglobin may involve Drabkin's Reagent (e.g. per Sigma Chemical Co. Cat #525-A). The volume of blood present in the obtained sample may also be determined on the basis of the measured level of any other blood component such as those mentioned above.

The amount of the tested analyte in the obtained sample is determined using any of the methods known in the art which are suitable for determining the level of the specific analyte to be tested. By a preferred embodiment of the invention the tested analyte is glucose. The level of the glucose in the body sample may be determined using any of the known highly sensitive glucose determination methods based on fluorescence, chemiluminescence, or bioluminescence. Examples of such methods are continuous monitoring of reactions that produce NADH and NADPH using immobilized luciferase and oxido reductases from *Beneckea harveyi* (Haggerty, C. et al., *Anal. Biochem.*, 88:162–173, 1978 or Jablonski, E., et al, *Clin. Chem.*, 25:1622–1627, 1979). In addition, any of the cholorimetric or electrochemical methods known in the art which utilize glucose oxidase or glucose dehydrogenase or hexokinase may also be used for determining the level of the glucose in the sample (see for example Sigma Cat #: 315, 115-A, 510-A).

Calculation of the concentration of the tested anlayte is based on the ratio of the concentration of the analyte which was measured in the obtained sample to the concentration of the blood component measured in the same sample and the average content of the same blood component in human blood. For example, wherein the tested analyte is glucose and the measured blood component is hemoglobin, the glucose concentration in the blood of the tested individual is calculated from the ratio of the glucose to hemoglobin which was measured in the obtained sample and the average hemoglobin contents in human blood.

The amount of the analyte in the blood of the tested individual will be calculated on the basis of the measurements of the blood volume and the level of the tested analyte in the obtained sample. Calibration values of the blood component and the tested analyte will typically be obtained from testing diluted standard solutions of these components by methods known in the art such as those described in the examples below. Typically, this will be carried out by dividing a body sample obtained from a tested individual into several aliquots; some being tested for the level of the tested analyte (e.g. glucose) by one or more of the tests known in the art and the remaining aliquots being tested for the level of the same analyte using the method of the invention. The results obtained by using the known methods and the results obtained by using the method of the invention are then correlated by using a standard regression analysis from which a regression equation having the following structure is obtained:
 level of tested analyte in the blood=(the level of the tested analyte measured by the method of the invention)×(slope)+(intercept);

wherein the slope and intercept values are derived from the regression analysis. Regression analysis can be easily performed by methods known in the art using software known to a person versed in the art such as, for example, Excel (Microsoft Corporation, Redmond, Wash.), Lotus 123, Quattro Pro, etc. Statistical software packages are also available such as, for example, the SPSS Program. In addition, regression functions are also incorporated into various hand-held calculators such as, for example, those manufactured by Texas Instruments, U.S.A., Hewlett-Packard, U.S.A., Casio, Japan, Sharp, Japan, etc.

By one embodiment of this aspect of the invention the non-blood body sample obtained from an individual to be tested is urine or saliva, which contain red blood cells and which comprise various analytes in their sap including detectable amounts of glucose. The obtaining of samples of urine and saliva does not inflict any harm to the tested individual and prevents the possible adverse side affects mentioned above. Thus such samples may be frequently and repetitively obtained without causing harm to the individual.

Wherein the obtained body samples are readily available body fluids such as blood or saliva, the tested analyte may originate from two sources: (a) fluid secreted by a gland or tissue or (b) from blood which contaminates the fluids in the samples. Therefore, in such cases, in order to determine the level of the tested analyte in the blood of the tested individual (e.g. glucose), the intercellular level of the tested analyte in the red blood cells present in the sample is measured. The amount of the blood component (typically hemoglobin), in the sample is also measured and both are used as a basis for determining the volume of the red blood cellular fluid.

In order to determine the level of the tested analyte in the obtained urine or saliva sample as well as the amount of the blood component in the sample, typically, the red blood cells present in the obtained samples are first separated.

Separation of the red blood cells from the obtained sample may be carried out by any of the methods known in the art such as centrifugation, or filtration. Alternatively, the samples may be applied onto a filter designed to trap red cells. Several non-limiting examples of such filters are the PlasmaSep™, filter obtained from Whatman®, Fairfield, N.J., U.S.A., the CytoSep® filter obtained from Ahlstrom Filtration, Mt. Holly Springs, Pa., U.S.A. or the HemaSep® filter obtained from Pall, East Hills, N.Y., USA. The trapped red cells are then tested for the level of the analyte and blood component. Optionally, the red cells may be lysed before testing for their contents. Some of these methods are described in the examples below but should not be construed as limiting.

Before separation of the red blood cells, an agglutinating agent such as, for example, wheat germ agglutinin may be added to the sample which causes agglutination of the red blood cells which may then be separated by any of the abovementioned methods. The intracellular level of the tested analyte will then be determined in the red blood cell. In accordance with one embodiment the separated red blood cells will first undergo a lysis step in order to release their contents.

Although, in most cases, it is preferred to first separate the red blood cells from the sample, at times, it may be preferred to lyse the cells without first separating them. In such a case, the sample will be divided into two specimens. To the first specimen, a lysis agent will be added which will cause lysis of the red blood cells whose contents will spill into the specimen. By subtracting the measured concentration of the tested analyte in the second specimen to which a lysis agent was not added, from the measured concentration of the analyte in the first specimen in which the red blood cells were lysed, it will be possible to determine the intracellular concentration of the analyte in the red blood cells (see sample 3 below).

Typically, a lysis agent will be added to the body sample at one of the stages of the method of the invention, but, at times, it may be possible to determine the intracellular concentration of the analyte in the red blood cells present in the sample without addition of a lysis agent. For example, wherein the sample is first run through a filter, the fixation of the cells onto the filter may cause ruptures in the cell membrane of the red blood cells and as a result their content may flow out of the cells and the level of the tested analyte is then determined.

Lysis of the red blood cells present in the samples may be carried out by any of the methods known in the art using known red cell lysing agents such as for example, saponin, ammonium salts, various detergents, hypotonic solutions, snake venoms, etc.

In accordance with this embodiment of the invention, the present invention provides a method for determining the level of an analyte in the blood of an individual comprising:
  (i) obtaining a urine or saliva sample from said individual;
  (ii) measuring the level of said analyte in the red blood cells present in said sample;
  (iii) measuring the amount of a blood component in the red blood cells in said sample and on the basis of this measurement calculating the volume of blood cells or number of blood cells in said samples; and
  (iv) calculating the level of said analyte in the blood of the tested individual based on the measurements in (ii) and (iii).

Wherein the body sample is saliva, it is possible, prior to obtaining the sample to use means which stimulate blood flow into the saliva such as swabs, brushes, toothpicks or various foods. In addition, in obtained saliva samples, before beginning measurements of the various substances in the obtained sample, it may be, at times, advantageous to remove or breakdown mucinaceous materials present in the sample by one of the methods described in the art) (such as, for example, U.S. Pat. No. 5,268,148).

The term "saliva" encompasses, in accordance with the invention, inter alia, saliva, diluted saliva, fluid obtained from the mouth cavity or from the skin surrounding the mouth cavity, scrapings attached from the surface of the mouth cavity, exudates or transudates obtained from the mouth cavity, and expectorated or drawn mouthwash obtained from the mouth cavity.

By a preferred embodiment of the invention, the above method will contain an additional step wherein the red blood cells are first separated from the sample by any of the methods described above. By another preferred embodiment, the method will comprise an additional step wherein a lysing agent will be added to the sample before the amount of the blood component and tested analyte are measured.

In accordance with an additional aspect of the invention the obtained body sample is hair roots.

According to the invention, it has been realized that there is a readily available naturally obtainable and sufficient source of fresh capillary blood in a hair root sample which may be used for determining the level of a tested analyte in the hair root as a basis for determining its level in the blood of the individual from which the hair roots were obtained. The hair follicle includes an extensive network of blood vessels which provide nourishment to the rapidly dividing hair root cells. A complex of entwined blood capillaries (papilla) enters the wide hair root at the bottom end of the hair and when the hair is plucked the blood rich papilla and sometimes the whole or part of the follicle's sheath is still attached to the hair shaft, thus providing a specimen of capillary blood. The capillary blood supply is of blood which reached the hair follicle only recently and therefore the level of the substance in the capillary blood very accurately represents that of the same substance in the individual's blood. Occasionally a tissue sample containing interstitial fluid may also be found on the plucked hair and used as a source for determining the level of an analyte in the blood. Since the interstitial fluid is in close proximity to abundant and active blood vessels of the hair root, the level of the analyte determined in this interstitial fluid is very indicative of the level of the same analyte in the blood at the same time.

Wherein the obtained body sample is hair roots, due to the extensive network of blood vessels in the hair root and hair sheath, it is expected that the whole amount of the tested analyte, e.g. glucose, in such a sample is derived from the fresh blood in the hair root. In addition, the origin of the measured blood component, typically being hemoglobin, in the hair may also be only the blood in the hair root. Since the concentration of the blood component in the blood of an individual is relatively constant, the concentration of the blood component measured in the fresh blood in the hair root is equal to its concentration in the blood of the tested individual. Therefore, it becomes possible to determine the concentration of the tested analyte (e.g. glucose) in the blood of the tested individual on the basis of the amount of the free analyte and amount of the blood component both extracted from the hair roots.

Contrary to the difficulties caused by repetitive puncturing of the skin, repetitive plucking of hair does not create any wound or scarring and the side effects as well as the individual discomfort are minimal, especially when a small number of hair shafts are being collected. In addition, a large fraction of the hair is naturally shed or easily removed by e.g. combing and such hair may also be obtained for use in accordance with the invention shortly after it is removed.

Thus, in accordance with an additional embodiment of this aspect of the invention, the level of a tested analyte in a blood of an individual is determined on the basis of the level of the analyte in a hair sample obtained from said individual. In accordance with this embodiment, the present invention thus provides a method for determining the level of an analyte in the blood of an individual comprising:
  (i) obtaining a sample of hair from said individual;
  (ii) determining the amount of blood or interstitial fluid in said obtained sample and if necessary, correcting variations between different hair samples;
  (iii) determining the level or concentration of said analyte in said blood or interstitial fluid; and
  (iv) calculating the level of said analyte in the blood of the tested individual based on the measurements in (ii) and (iii).

In accordance with this embodiment of the invention, the sample of hair may be obtained by any of a number of methods, e.g. by use of a hair removal instrument, adhesive strips, a forceps, by combing, etc.

Before determining the amount of the blood or interstitial fluid in the hair follicle, these may be extracted from the hair follicle by incubating the obtained hair in a suitable diluent such as, for example, buffered saline. The diluent may include components which will enhance its extracting capacity, such as, for example, anticoagulants (e.g. heparin, citrate, EDTA), enzymes (e.g. proteases, neuroaminidases), keratolytic agents (benzoic and/or salicylic acids or their salts), and detergents.

The remaining steps of the method of the invention carried out on the hair root specimen will be similar to the steps described above with regards to other kinds of body samples and fluids. However, in this case, a separation step of red blood cells is not necessary since the only origin of the tested analyte is in the blood extracted from the hair root. Notwithstanding the above, it may at times be advantageous to add a lysing agent to the sample extracted from the hair root to facilitate the measurement of the tested analyte and blood component in the sample.

By an additional aspect of the invention, a kit is provided for determining the level of an analyte in the blood of a tested individual comprising:
  (i) means for obtaining a sample from said individual, said sample being a non-blood sample but containing blood components;
  (ii) means for measuring the level of a blood component in the sample;
  (iii) means for measuring the level of the tested analyte in the obtained sample;
  (iv) means for calculating the level of the tested analyte in the blood of the tested individual on the basis of the measurements obtained in (ii) and (iii) above.

By one embodiment of this aspect of the invention, the above kit will also comprise means for separating the red blood cells from the sample, which may be any one of those discussed above. By an additional embodiment, the kit may also comprise means for lysing the red blood cells in the sample such as, for example, any of those detailed aove.

The above kit may also comprise a test strip incorporating the reagents or structures necessary to carry out the measurement of the tested analyte as well as the blood component. In such a case, an instrument into which the test strip can be inserted or to which the test strip may be connected is also included in the kit. Such an instrument, which may be portable, is capable of detecting and analyzing the signal emitted by the test strips and optionally may translate them directly into prevalent units.

Wherein the obtained body fluid sample is saliva, the above kit may also include means to stimulate blood flow into the saliva such as swabs, brushes, toothpicks or stimulating pieces of food which are applied to the tested individual before obtaining a body sample. The above kit may then also include reagents and means capable of removing or breaking down the mucinaceous materials present in the saliva (such as those mentioned above) for treating the saliva sample prior to analysis or testing.

Wherein the tested analyte is glucose, the above kit may also comprise a metabolic inhibitor such as, for example, sodium fluoride which is capable of preventing glucose utilization by any living cell contained in the sample.

In accordance with the embodiments of the invention in which the obtained body sample is a hair sample, the kit of the invention will comprise the following:
  (i) a hair removal instrument;
  (ii) a suitable diluent in which the blood or interstitial fluid from the obtained hair is collected;
  (iii) means for the determination of the level of a blood component in the blood or interstitial fluid specimen;
  (iv) means for determination of the level of said analyte in the blood or interstitial fluid specimen; and
  (v) means for calculating the level of the tested analyte in the blood of the tested individual on the basis of the measurements in (iii) and (iv) above.

EXAMPLES

The invention will now be demonstrated by way of the following non-limiting examples.

Example 1

Determination of the Level of Glucose and Hemoglobin in a Sample Obtained from a Hair Follicle in Accordance with the Invention Obtaining a Sample from Hair of a Tested Individual About 5–10 hair strands are plucked by pulling on any hairy skin area (scalp, hands, legs, face, nose, ears, etc.). The hair is then washed in water and immersed in 500 µL of Sigma Chemical Co. (St. Louis. MO, USA) red cell lysing agent (Cat #R1129).

The hair is incubated in the above solution for a period of time suitable for obtaining the maximum volume of blood and its interstitial fluid from the hair. The fluid sample is then divided into the following two samples:

a. A Sample Used for Determining the Level of Glucose in the Obtained Blood or Interstitial Fluid In a micro-centrifuge ("Eppendorf" style) test tube, 25 µL of the above sample is mixed with 100 µL of a glucose oxidase, horseradish peroxidase mix, prepared from the enzyme capsule in Sigma Chemicals calorimetric glucose test kit (cat #510-A or 510-DA). Following 10 minutes incubation at room temperature (18–30° C.), a hundred µL of 1:1 diluted Pierce (Rockford, Ill., USA) POWERSIGNAL™ Luminol/Enhancer (derived from cat #37075) are then added and incubation continued for another 1 minute. The test tube is then inserted into a Labsystems LUMINOSKAN luminometer and the luminescence is recorded.

b. Sample 2 is Used for Determining the Level of Hemoglobin in the Blood and Interstitial Fluid Obtained from the Hair of the Tested Individual In a micro-centrifuge ("Eppendorf" style) test tube, 25 µL of the above sample is mixed with 100 µL of Pierce POWERSIGNAL™ ELISA Chemiluminescent Substrate Working Solution, prepared according to the instructions of product #37075. Following 1 minute of incubation, the test tube is then inserted into Labsystems LUMINOSKAN luminometer and the luminescence is recorded.

c. The Levels of the Glucose and Hemoglobin in the Sample Obtained from the Hair of the Tested Individual is then Calculated as Follows:

The net glucose reaction is derived from the above glucose luminescence minus the hemoglobin luminescence. The actual glucose and hemoglobin content of the hair sample is calculated employing the calibration equation. The glucose concentration in the blood is calculated from the ratio of glucose to hemoglobin in the sample and the average hemoglobin contents of human blood.

d. The Glucose and Hemoglobin Values were Calibrated as Follows:

Glucose and hemoglobin calibration values were obtained from testing diluted standard glucose and hemoglobin solutions, employing the above procedures. A calibration equation is derived from the results and employed in the above calculations.

Example 2

Determination of the Level of Glucose and Hemoglobin in a Urine or Saliva Body Sample using Luminescent Method Involving Centrifugation About 500 µL of urine or saliva are mixed with 500 µL of 0.85% saline and centrifuged in a Microfuge (Eppendorf or other) for 5 minutes to spin down the red cells. The supernatant is decanted and the cell sediment is washed in saline and then resuspended in a buffer solution containing a red cell lysing agent or Sigma Chemical Co (St. Louis, Mo. USA) red cell lyzing agent (Cat#R 1129).

Following the required incubation period, two aliquots are removed. One of the aliquots is subjected to glucose analysis and the other - to hemoglobin analysis.

The level of glucose in the first aliquot is then determined as follows:

In a micro-centrifuge ("Eppendorf" style) test tube, 25 µL of the above sample is mixed with 100 µL of a glucose oxidase, horseradish peroxidase mix, prepared from the enzyme capsule in Sigma Chemicals calorimetric glucose test kit (Cat #510-A or 510-DA). Following 10 minutes incubation at room temperature (18–30° C.), a hundred µL of 1:1 diluted Pierce (Rockford, Ill., USA) POWERSIGNAL™ Luminol/Enhancer (derived from Cat #37075) are then added and incubation continued for another 1 minute. The test tube is then inserted into a Labsystems LUMINOSKAN luminometer and the luminescence is recorded.

The level of hemoglobin in the second aliquot is then determined as follows:

In a micro-centrifuge ("Eppendorf" style) test tube, 25 µL of the above sample is mixed with 100 µL of Pierce POWERSIGNAL™ ELISA Chemiluminescent Substrate Working Solution, prepared according to the instructions for product #37075. Following 1 minute of incubation, the test tube is then inserted into a Labsystems LUMINOSKAN luminometer and the luminescence is recorded.

Calibration values and calculations are determined as explained in Example 1 above.

Example 3

Determination of the Level of Glucose and Hemoglobin in a Urine or Saliva Body Sample Using the Lysis Method Equal size aliquots are derived from the urine or saliva sample. One of the aliquots is mixed with a reagent, which causes the lysis of red blood cells such as, for example, saponin. Another aliquot is mixed with the same volume of a non-lytic reagent. The levels of glucose and hemoglobin are determined in both aliquots. The amount of glucose and hemoglobin in the red cells sap is obtained by substracting the values of the non-lysed aliquot from the lysed one.

Example 4

Determination of the Level of Glucose and Hemoglobin in a Urine or Saliva Body Sample Using the Filtration Method Urine or saliva sample is applied to a filter, designed to trap red cells. The sample is sucked through the filter by e.g. application of vacuum or providing an absorbent pad under the filter (such absorbent materials are very well known in the art: Polyfiltronics, AFC (American Filtrona Corp). The filter is then subjected to glucose and hemoglobin tests. The endpoint signal of the tests can be calorimetric, fluorometric, luminescent, electrochemical, radioactive (non-limitative list of endpoints), all are well known in the art.

In alternative embodiments of the filtration method:

A. The filter can be impregnated with reagents for hemoglobin (e.g. as in urine test strips, supplied by Bayer Corp. (U.S. Pat. No. 5,089,420) or Lachema a.s., Brno, Czech Republic. U.S. Pat. Nos. 3,975,161 and 4,017,261) and glucose.

B. Individual red cells can be visualized on the filter (as in the above mentioned urine test strips) and the signal that develops with each cell can be individually examined e.g. with a microscope and/or camera with macro lens.

The invention claimed is:

1. A method for determining the level of glucose in blood from a non-blood sample from an individual comprising:
   (i) obtaining a sample of hair or urine from said individual, said sample being a non-blood sample but containing blood components;
   (ii) determining the volume of blood in the obtained sample by measuring the level of hemoglobin in said sample;
   (iii) determining the amount of glucose in the sample or in blood cells present in said non-blood sample; and
   (iv) calculating the level of glucose in the blood of the individual based on the measurements in (iii) and (iv).

2. The method according to claim 1, wherein said non-blood sample is a sample of hair obtained from said individual, the method comprising:
   (i) obtaining a sample of hair from said individual;
   (ii) determining the amount of blood and interstitial fluid, if present, in said obtained sample and if necessary, correcting variations between different hair samples;
   (iii) determining the level of glucose in said blood and interstitial fluid, if present and
   (iv) calculating the level of glucose in the blood of the tested individual based on the measurements in (ii) and (iii).

3. The method according to claim 2 wherein before stage (ii) said blood and interstitial fluid, if present, are first extracted from a hair follicle of said obtained hair.

* * * * *